United States Patent [19]

Hoyle

[11] Patent Number: 5,332,678
[45] Date of Patent: Jul. 26, 1994

[54] PROCESS FOR LIBERATING AN ANALYTE FROM ITS BINDING PROTEIN

[75] Inventor: Nicholas R. Hoyle, Tutzing, Fed. Rep. of Germany

[73] Assignee: Boehringer Mannheim GmbH, Mannheim-Waldhof, Fed. Rep. of Germany

[21] Appl. No.: 463,188

[22] Filed: Jan. 10, 1990

[30] Foreign Application Priority Data

Jan. 11, 1989 [DE] Fed. Rep. of Germany ....... 3900649

[51] Int. Cl.$^5$ ............................................... G01N 1/00
[52] U.S. Cl. ..................................... 436/175; 436/174; 436/86; 436/119
[58] Field of Search ................ 436/174, 175, 86, 119, 436/177, 825, 17

[56] References Cited

U.S. PATENT DOCUMENTS

| | | | |
|---|---|---|---|
| 4,100,150 | 7/1978 | Cartwright | 530/351 |
| 4,429,008 | 1/1984 | Martin et al. | 436/501 |
| 4,545,988 | 10/1985 | Nakayama et al. | 435/215 |
| 4,714,611 | 12/1987 | Yasaburgo et al. | 435/69.51 |
| 4,767,204 | 8/1988 | Cleveland | 435/30.2 |
| 4,780,281 | 10/1988 | Marnett et al. | 435/28 |
| 4,784,804 | 11/1988 | Basch et al. | 436/501 |
| 4,806,524 | 2/1989 | Kawaguchi et al. | 514/8 |
| 4,812,557 | 3/1989 | Yasushi et al. | 435/69.51 |
| 4,902,495 | 2/1990 | Kaliner et al. | 530/402 |
| 4,978,613 | 12/1990 | Bieniarz et al. | 435/4 |
| 4,981,979 | 1/1991 | Sivam | 436/544 |

FOREIGN PATENT DOCUMENTS

| | | |
|---|---|---|
| 8203461 | 10/1982 | PCT Int'l Appl. . |
| 8905975 | 6/1989 | PCT Int'l Appl. . |
| 2084320 | 4/1982 | United Kingdom . |

OTHER PUBLICATIONS

The Condensed Chemical Dictionary-10th Edition, 1981 p. 1019.
The Merck Index-10th Edition, 1983, pp. 493 and 1336.
Silverman, R. B.; Nandi, D. L.; "Reduced Thioredoxin: A Possible Physiological Cofactor for Vitamin K Epoxide Reductase. Further Support for an Active Site Disulfide", Biochem. Biophys. Res. Commun, 155(3) pp. 1248-1254 Sep. 30, 1988.
Pettit, F. H.; Humphreys 5; Reed, L.J.; "Regulation of Pyruvate Dehydrogenase Kinase Activity by Protein Thiol-Disulfide Exchange"; Proc Natl Acad Sci USA, (1982 Jul) 79(13) 3945-8.
STN-File Biosis Accession No. 76:226983 Iordan et al; "Ribo Nucleotide Reductase of Propioni-Bacterium-Shermanii"; Mikrobiologiya 44(4)-1975 pp. 609-614.

*Primary Examiner*—James C. Housel
*Assistant Examiner*—Maureen M. Wallenhorst
*Attorney, Agent, or Firm*—Felfe & Lynch

[57] ABSTRACT

A process for the dissolving off of an analyte bound to a binding protein by breakdown of the binding protein using a cleaving agent which cleaves —S—S— groups into SH groups in the alkaline range, wherein a 1,2-dithiolan-3-carboxylic acid of the formula:

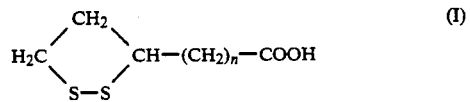

is used as the —S—S— group cleaving agent in which n is a whole number of from 1 to 8. The process is used for preparing samples for analytical or investigational processes for the determination of a liberated analyte and especially for immunoassays for vitamins such as vitamin $B_{12}$, steroids such as testosterone or for thyroid hormones such as $T_3/T_4$.

9 Claims, 1 Drawing Sheet

PROCESS FOR LIBERATING AN ANALYTE FROM ITS BINDING PROTEIN

The present invention is concerned with a process for the dissolving off of an analyte bound to a binding protein from this binding protein by the breakdown of the binding protein by a thiol cleaving —S—S— groups.

Many interesting analytes, for example vitamins and steroids, are bound specifically or non-specifically to binding proteins, for example serum proteins and other natural binding materials. Before they can be determined, the analytes must be dissolved off from their binding proteins or other binding materials. In many cases, this can be achieved by the use of the competition principle, for example by the addition of an excess of cross-reactive analogues of the analyte or by maintaining mild dissociative conditions, for example by the addition of 8-anilino-1-naphthalenesulphonic acid (ANS) in order to dissolve off $T_4$ from thyroxine-binding globulin (TBG). However, in some cases, the binding is so strong that stronger methods of breakdown are necessary, such as for example for dissolving off vitamin $B_{12}$.

The methods at present conventional for the determination of analytes, for example of vitamin $B_{12}$ (cyanocobalamine) in highly diluted aqueous solutions, for example in blood serum, are based on processes using radio-actively labelled materials in which intrinsic factor (IF) is used as binding agent. The conventional techniques work with the use of $^{57}Co.B_2$ as label on the basis of a competitive principle in which free and labelled analyte compete for the binding to the IF. The separation of the bound and free samples (bound/free separation) then takes place on the basis of methods in which the IF is bound to paramagnetic particles, such as for example with the use of active carbon, solid phase-bound IF or magnetic separation.

The methods which are at present conventional for dissolving off the analyte, for example of vitamin $B_{12}$, from serum binding protein (sample preparation), are usually based on the destruction of the binding protein in the alkaline range (pH 13.5) with the action of the thiol dithiothreitol (DTT) cleaving the —S—S— groups (incubation of the serum sample by means of DTT in the alkaline range) or by boiling for 30 to 60 minutes and subsequent centrifuging. This destruction can be reinforced by the addition of organic materials, for example acetone, alcohol or the like, or by the addition of competitive, cross-reacting species, for example of cobinamide. Furthermore, all the usual test methods contain potassium cyanide in order to increase the extractability of vitamin $B_{12}$ and in order to convert the cobalamine into a uniform, stable and detectable form, namely into cyanocobalamine.

Disadvantages of these techniques of sample preparation which are at present conventional are, in particular, in the case of the use of DTT, the small dissolving off effectiveness (only about 60 to 80%), limited stability and unpleasant smell. In the routine laboratory, the dissolving off by heating is impracticable due to the necessary technical expense and the time required for the boiling and centrifuging.

Therefore, it is an object of the present invention to provide a process for the preparation of the sample with which the above-mentioned deficiencies of the methods hitherto conventional for the sample preparation can be overcome.

Thus, according to the present invention, there is provided a process for the dissolving off of an analyte bound to a binding protein by the breakdown of the binding protein by means of a thiol cleaving —S—S— groups in the alkaline range, wherein, as thiol cleaving —S—S— groups, there is used a 1,2-dithiolane-3-carboxylic acid of the general formula:

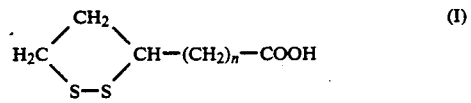

wherein n is a whole number of from 1 to 8 and preferably of from 3 to 5.

As acid of general formula (I), there is preferably used lipoic acid. As alkaline medium, there is advantageously used a solution of an alkali metal hydroxide, preferably a solution of sodium or potassium hydroxide. The concentration of alkali is thereby preferably in the range of from 0.05 to 1 mole/liter. The preferred concentration of the carboxylic acid of general formula (I) is from 1 to 20 mg/ml and preferably from 4 to 10 mg/ml (calculated for lipoic acid with n =4).

The process according to the present invention is, in principle, suitable for the dissolving off of all analytes which are present bound to specific binding proteins and especially for the dissolving off of vitamins, thyroid hormones or steroids. The process according to the present invention has proved to be especially suitable for the liberation of vitamin $B_{12}$ as analyte.

According to a preferred embodiment of the present invention, the process is carried out in the presence of potassium cyanide. The concentration of the potassium cyanide is advantageously from 1 to 10 mg/ml but greater or smaller concentrations can also already lead to a further improvement of the dissolving off.

In the above general formula (I), n is preferably 3 to 5 and is especially 4 (lipoic acid).

As alkaline medium, there is preferably used an alkali metal hydroxide and especially sodium or potassium hydroxide. The concentration of the alkali is thereby advantageously in the range of from 0.05 to 1 mole/liter and preferably from 0.2 to 0.7 mole/liter. The pH value of the medium is thereby at least 10, generally from 10 to 14, preferably from 13 to 14 and especially preferably 13.6.

The 1,2-dithiolane-3-carboxylic acid of general formula (I) is (calculated for lipoic acid with n=4) preferably in the range of from 1 to 20 mg/ml and especially in the range of from 1 to 20 mg/ml and especially in the range of from 4 to 10 mg/ml and in particular of from 5 to 8 mg/ml. For the determination of vitamin $B_{12}$, it is preferred to work in the presence of a cyanide, for example of potassium cyanide. The cyanide is advantageously used in an amount of from 0.5 to 5 mg/ml and especially of 1 mg/ml.

The process according to the present invention for the preparation of samples can be used not only for manual determination processes but also for processes making use of automatic analyzers.

The advantages of the process according to the present invention are especially the following: the destruction of the binding protein takes place very quickly and, as a rule, in less than 15 minutes; the process is very efficient, with a dissolving off of 80 to 95%; the reagent solution for the preparation of the sample is very stable, the storage stability at ambient temperature being more than 8 weeks; with the use of the dissolving off reagent according to the present invention, no unpleasant smell arises and the reagent is completely non-toxic; the reagent can be used universally; due to the tendency of lipoic acid to bind to the proteins while it destroys them, the influencing of the test is very small and the possibility of the reformation of the protein and analyte complexes in the case of making the pH value neutral is very considerably limited.

The process according to the present invention for dissolving off an analyte bound to a binding protein from this binding protein is suitable for the preparation of samples for a large number of methods of determination. The process according to the present invention is preferably used for analytes such as vitamins, thyroid hormones and steroids, for example for dissolving off testosterone from testosterone-binding globulins; $T_3$ and $T_4$ from thyroxine-binding globulins (TBG) but also for other systems in which the analyte is bound to a protein, for example a tumour label bound to a cell matrix or binding protein and especially for the preparation of samples in processes for the determination of vitamin Processes for the determination of such analytes are described, for example, in K. Lübke, Immunologische Teste fü niedermolekulare Wirkstoffe, pub. Georg Thieme Verlag, Stuttgart (1978); Clin. Chem. Acta., 22 51–69/1968; B. Rothfeld ed. Nuclear Medicine, pub. Lippincott, Philadelphia, 69–84, 1974, as well as for especially testosterone in J. Endocr., 100, 367–376/1984; J. Steroid. Biochem., 19, 1605–1610/1983; as well as J. Steroid, Biochem., 22, 169–175/1985 and published Federal Republic of Germany Patent Specification No. 35 45 252. Processes for the determination $T_3$ and $T_4$ are described, for example, in Biochem. Biophys. Res. Comm., 46, 2107–2113/1972. Processes for the determination of vitamin $B_2$ are described, for example, in Clinical Biochemistry, 18, 261–266/1985; J. Clin. Path., 20, 683–686/1967; Brit. Haemat., 22, 21–31/1972; Biochem. Biophys. Res. Comm., 46, 2107–2113/1972, as well as in Federal Republic of Germany Patent Application P 39 00 650.6 (title "Vitamin $B_{12}$ determination" (published Jul. 12, 1990)) of the same applicant and with the same application date, the contents of which are also part of the disclosure of the present Application.

The present invention also provides a reagent for the carried out for 15 minutes at ambient temperature in the alkaline range and neutralized before carrying out process step c). Instead of potassium cyanide, there can also be used sodium cyanide or some other easily dissociating cyanide with a cation which does not influence the process.

As competitively labelled $B_2$ (label) in step d), there can be used, for example $^{57}Co.B_{12}$. In order to avoid the disadvantages involved with the use of radioactive labels, there is advantageously used $B_{12}$ conjugate of the general formula:

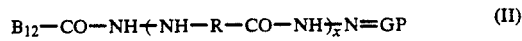

wherein $B_{12}$ is the residue formed from cyanocobalamin (vitamin $B_{12}$) by splitting off a $-CONH_2$ group and R is a spacer and x is 0 or 1 and GP is the residue of a glycosyl group-containing labelling enzyme which is bound via a glycosyl radical to the $-NH-N=$ grouping. In general formula (II), the $-CONH-$ grouping is preferably in the d-position of the $B_{12}$ residue; preferably there are used $B_{12}-d-CO-NH-N=GP$ and especially $B_{12}-d-CO-NH-NH-CO-CH_2-(O-CH_2-CH_2-)_3O-CH_2-CO-NH-N-GP$, in which GP is the peroxidase residue (POD).

The $B_{12}$ conjugates of general formula (II) are the subject of Federal Republic of Germany Patent Application P 39 00 648.4 (title "New cobalamine acid hydrazides and cobalamine acid hydrazides derived therefrom) of the same Applicant and with the same application date (published Jul. 12, 1990). They can be prepared by the coupling (condensation) of cobalamine acid hydrazides of the general formula:

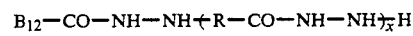

wherein $B_{12}$, R and x have the above-given meanings, which are also the subject of the above-mentioned simultaneously filed Federal Republic of Germany Patent Application P 39 00 648.4, with the hydroxyl groups of glycosyl residues of glycoproteins after the oxidation thereof and formation of the hydrazone grouping $-NH-N=CH-$ glycoprotein under known conditions.

As labelling analyte, there is especially preferably used:

preparation of samples for the determination of vitamin $B_{12}$ in blood serum, which reagent contains 1 to 20 mg/ml lipoic acid and 1 to 10 mg/ml of an alkali metal cyanide at a pH of from 10 to 14.

The reagent for the preparation of the sample is added to the sample and incubated therewith for preferably 10 to 20 minutes and especially for 15 minutes at ambient temperature. Subsequently, the pH value is lowered to a value of from 7 to 9. This is preferably carried out slowly and especially in two steps with the use of appropriate buffer solutions since otherwise precipitation could occur.

According to the process of the present invention, the sample preparation preferably takes place with the use of lipoic acid (general formula (I), n=4). It is advantageous to work in the presence of potassium cyanide, preferably at a concentration of 1 to 10 mg/ml and especially of 1 to 5 mg/ml. The incubation is preferably The determination of the POD can take place in known manner. The determination of the POD advantageously takes place via a color reaction of POD with the diammonium salt of 2,2'-azino-di(3-ethylbenzthiazoline-6-sulphonic acid) (ABTS) as chromogen.

The pretreatment of the sample (step b)) can take place externally or also in the scope of an automatic vitamin $B_{12}$ determination program, for example with the use of the above-mentioned automatic analysis apparatus. The amount of $B_{12}$ conjugate, which can be used in solution, as concentrate or also in lyophilized form, is especially dependent upon the nature of the sample and the $B_{12}$ content to be expected therein. The optimum amount is advantageously previously determined for a particular $B_{12}$ content to be expected.

With the process for the determination of vitamin $B_{12}$ with the use of the sample preparation according to the present invention, especially with the simultaneous use of the above-mentioned antibody as binding reagent for vitamin $B_{12}$, a test system is made available with which the problems which arise in the case of the use of the previously conventional sample preparation in combination with radioactively-labelled $B_{12}$ are avoided. The system according to the present invention is not dangerous to health and the reagents display a substantially greater storage stability than is the case with the previously conventional test systems. Due to the easy handling and lack of danger of the reagents employed, and the simple carrying out of the test, the system is, in all, user friendly. The monoclonal antibodies employed are not influenced by serum antibodies which can bind or block the previously used IF. The use of the dissolving off method (sample preparation) according to the present invention contributes to the improvement of the exactitude of the test and to the greater acceptance of the test. A better reproducability and a greater efficiency of the dissolving off of vitamin $B_{12}$ is achieved.

The following Examples and the accompanying drawing are given for the further explanation of the present invention, without limiting it thereto. Ambient temperature is to be understood to be a temperature of $25 \pm 2°$ C. Statements of percentage are percentages by weight.

BRIEF DESCRIPTION OF THE DRAWING

The Figure shown in the accompanying drawing shows standard curves for the determination of vitamin $B_{12}$ without addition (curve 1), with the addition of 10 mg/ml lipoic acid (curve 2) and with the addition of 10 mg/ml DTT (curve 3).

It will be understood that the specification and examples are illustrative but not limitative of the present invention and that other embodiments within the spirit and scope of the invention will suggest themselves to those skilled in the art.

EXAMPLE 1

Sample Preparation with Lipoic Acid

Figure 1:
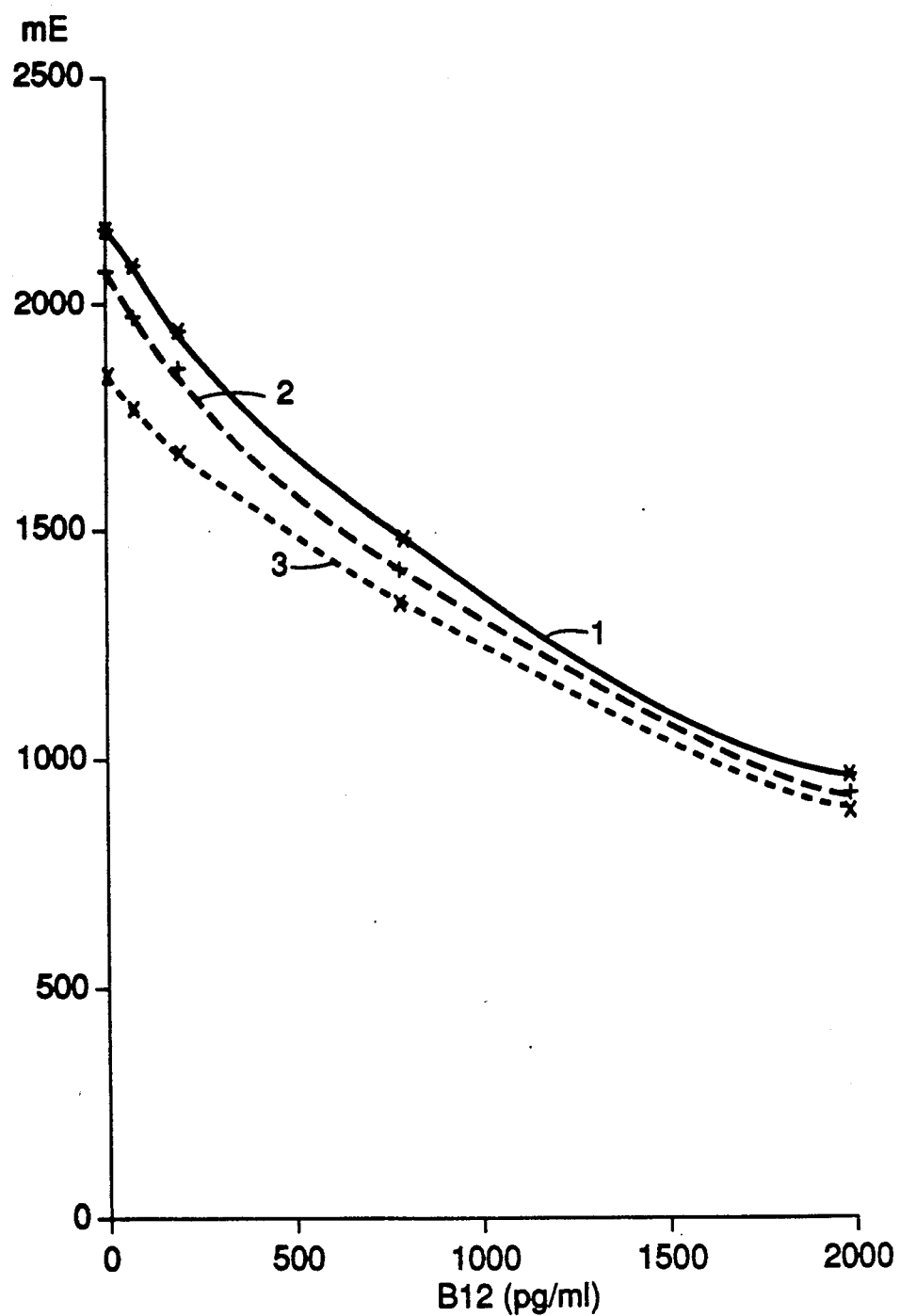

250 μl of human serum are mixed with 125 μl of dissolving-off reagent, consisting of 8 mg/ml lipoic acid, 1 mg/ml potassium cyanide dissolved in 0.5 mole/liter sodium hydroxide solution, and incubated for 15 minutes at ambient temperature. Subsequently, 125 μl of 200 mmole/liter phosphate buffer (pH 4.1) are added thereto.

Instead of 200 mmole/liter of phosphate buffer (pH 4.1), there can also be used 25 μl of 1.5 N phosphoric acid. This has the advantage that the dilution of the sample is thereby reduced.

In a further variant, 800 μl of phosphate buffer (200 mmole/liter; pH 7.2) can be added for the neutralization.

EXAMPLE 2

Sample Preparation with DTT (Comparison)

250 μl of human serum are mixed with 125 μl of dissolving-off reagent, consisting of 10 mg/ml DTT and 1 mg/ml potassium cyanide dissolved in 0.5 mole/liter sodium hydroxide solution, and incubated for 15 minutes at ambient temperature. Subsequently, 125 μl of phosphate buffer (200 mmole/liter; pH 4.1) are added thereto.

EXAMPLE 3

Determination of Vitamin $B_{12}$ a) Reagents

Polystyrene test tubes coated with thermobovine serum albumin streptavidin, prepared according to published European Patent Specification No. 0,269,092.

Reagent 1

95 ng/ml biotinylated monoclonal antibody ("MAB") against vitamin $B_{12}$ (ECACC 88101302) (biotinylation according to J.A.C.S., 100, 3585–3590/1978)
40 Mole/liter phosphate buffer, pH 7.2

Reagent 2

$B_{12}$—d—CO—NH—NH—CO—CH$_2$—(O—CH$_2$—CH$_2$)$_3$—O—CH$_2$—CO—NH—N—POD (activity about 60 mU/ml)
40 mmole/liter phosphate buffer, pH 7.2).

Reagent 3

100 Mole/liter phosphate-citrate buffer, pH 4.4
1.9 mmole/liter ABTS ®(2,2′-azino-di[3-ethylbenzthiazoline-sulphonate])
3.2 mmole/liter sodium perborate b). Carrying Out of the Determination

For carrying out the determination 200 μl of sample pretreated according to Example 1 or 2 are introduced into a streptavidin tube with 800 μl of Reagent 1 and incubated for 60 minutes at ambient temperature. Washing subsequently carried out with a wash solution (250 mg/ml sodium chloride, 1 mg/100 ml copper sulphate), 1000 μl of Reagent 2 added thereto and incubated for 30 minutes at ambient temperature. It is again washed with wash solution (250 mg/ml sodium chloride and 1 mg/100 ml copper sulphate) and Reagent 3 added thereto, incubated for 30 minutes at ambient temperature and the color formed measured at 420 nm as a measure for the content of vitamin $B_{12}$.

The following Table 1 shows a comparison of the results for different human sera in the case of the use of lipoic acid or DTT as dissolving-off reagent in the test according to Example 3:

TABLE 1

| $B_{12}$ concentration (pg/ml) | |
| --- | --- |
| lipoic acid 10 mg/ml | DTT 10 mg/ml |
| 376 | 94 |
| 452 | 174 |
| 418 | 252 |
| 513 | 152 |
| 3939 | 458 |

It follows therefrom that, in the case of the use of lipoic acid, higher measurement values and thus a better dissolving off can be achieved.

FIG. 1 shows, in the case of the use of cyanocobalamine standard (cyanocobalamine in 40 mmole/liter phosphate buffer, pH 7.2, with 0.9% sodium chloride, 0.9% crotein C and 0.1% potassium cyanide), the influence of DTT (10 mg/ml) and lipoic acid (10 mg/ml) on the calibration curve. According to this, the calibration curve is only very slightly influenced by lipoic acid.

Analogous results are obtained when, as MAB against $B_{12}$, there is used a MAB from the cell line ECACC 88101301.

EXAMPLE 4

Testosterone Determine

Reagents

Test Buffer 35 ng/ml of monoclonal antibody against testosterone (ECACC 85121701), 40 mmole/liter sodium phosphate, pH 6.8.

Loading Solution

10 μg/ml polyclonal sheep antibody (IgG) against mouse Pc-gamma
20 mmole/liter sodium carbonate buffer (pH 9.6).

Wash Solution 250 mg/100 ml sodium chloride
1 mg/100 ml copper sulphate

Substrate Solution 1.9 mmole/liter ABTS®(2,2''-azino-di[3-ethylbenzthiazoline-6-sulphonic acid]diammonium salt)
100 mmole/liter phosphate-citrate buffer (pH 4.4)
3.2 mmole/liter sodium perborate Sample Human serum pretreated with lipoic acid according to Example 1 or with DTT according to Example 2.

For carrying out the determination 1 ml of loading solution was incubated for 30 minutes at ambient temperature in a Luran test tube. Subsequently, the tube was washed twice with wash solution, 1 ml test buffer was added, incubated for 30 minutes at ambient temperature and washed twice with wash solution. 100 μl of sample and 1 ml testosterone 3-cmo-POD conjugate (prepared according to Federal Republic of German Patent Specification No. 38 33 149 (published Apr. 5, 1990; U.S. Pat. No. 4,990,443 issued Feb. 5, 1991); 80 mU/ml) in 40 Mole/liter sodium phosphate buffer (pH 6.8) with 0.2% Pluronic F68, were added thereto, incubated for 30 minutes at ambient temperature and washed twice with wash solution. Thereafter, 1 ml of substrate solution was added thereto, incubated for 30 minutes at ambient temperature and the extinction measured at 405 nm.

I claim:

1. A process for liberating an analyte bound to a binding protein consisting of breaking down the binding protein by an agent which cleaves S—S bonds in said protein into SH groups in an alkaline range of pH 10–14, wherein the analyte is selected from the group consisting of vitamin $B_{12}$, $T_3$, $T_4$ and testosterone and the S—S group-cleaving agent is lipoic acid.

2. Process of claim 1 wherein the alkaline range of pH 10–14 is produced by an alkali metal hydroxide.

3. Process of claim 2 wherein the alkali metal hydroxide is sodium hydroxide or potassium hydroxide.

4. The process of claim 3 wherein the alkali concentration is from 0.05 to 1 mole/liter.

5. Process of claim 2 wherein the alkali concentration is from 0.05 to 1 mole/liter.

6. Process of claim 1 wherein the concentration of lipoic acid is in a range of from 1 to 20 mg/ml.

7. Process of claim 6 wherein the concentration of lipoic acid is in a range of from 4 to 10 mg/ml.

8. Process of claim 1 wherein the analyte liberated is vitamin $B_{12}$ in the presence of potassium cyanide.

9. Process of claim 8, wherein the concentration of potassium cyanide is from 1 to 10 mg/ml.

* * * * *

UNITED STATES PATENT AND TRADEMARK OFFICE
CERTIFICATE OF CORRECTION

PATENT NO. : 5,332,678
DATED : July 26, 1994
INVENTOR(S) : Nicholas R. Hoyle

It is certified that error appears in the above-indentified patent and that said Letters Patent is hereby corrected as shown below:

Col. 1, line 30: change "conventionai" to -- conventional --.

Col. 3, line 23: after "vitamin" insert -- $B_{12}$. --.

Col. 3, line 26: change "fü" to -- für --.

Col. 3, line 37: change "B,2" to -- $B_{12}$ --.

Col. 4, line 7: change "$B_2$" to -- $B_{12}$ --.

Signed and Sealed this

Eighth Day of November, 1994

BRUCE LEHMAN

Attest:

Attesting Officer

Commissioner of Patents and Trademarks